US00PP14758P2

(12) United States Plant Patent
van Os

(10) Patent No.: US PP14,758 P2
(45) Date of Patent: May 4, 2004

(54) ROSA PLANT NAMED 'SELQUEST'

(50) Latin Name: *Rosa L.*
Varietal Denomination: Selquest

(75) Inventor: Diana Petronella Maria van Os, Bleiswijk (NL)

(73) Assignee: Terra Nigra Holding BV, Kwakel (NL)

( * ) Notice: Subject to any disclaimer, the term of this patent is extended or adjusted under 35 U.S.C. 154(b) by 11 days.

(21) Appl. No.: 10/307,573

(22) Filed: Dec. 2, 2002

(51) Int. Cl.[7] ..... A01H 5/00
(52) U.S. Cl. ..... Plt./139
(58) Field of Search ..... Plt./139

*Primary Examiner*—Anne Marie Grunberg
*Assistant Examiner*—Susan B. McCormick

(57) ABSTRACT

A new rose of the Hybrid Tea class, characterized by its continuous producton of flowers of a stable dark red not affected by climatical changes, having a very good presentation in bud as well as open flower, borne singly on upright long stems, especially adapted to the South American climate.

1 Drawing Sheet

BACKGROUND OF THE INVENTION

The present invention relates to a new and distinct variety of rose plant of the Hybrid Tea class, which was originated by me by crossing the unnamed seedling SR90.204 (not patented, seed parent) with Black Magic (not patented, pollen parent). The female parent is also red with a smaller flower, having an extremely good vase life. The male parent is also red but has more shiny foliage compared to the present invention. This crossing was carried out In a greenhouse In De Kwakel.

The primary objective of this breeding was to obtain a new hybrid-T type rose with a good presentation and bud-shape in red, not suffering from cold or hot temperatures. Among the novel characteristics possessed by the new variety which distinguish it from its parents and all other varieties of which I am aware are:

1) A very large flower and flowerbud.
2) The persistent red color of the flower.
3) Vigorous growth of the plant.
4) Long flower stems.
5) Suitability for growing in especially South American countries.

Asexual reproduction of the new rose variety by cutting and grafting using 'Natal Briar' (not patented) as rootstock, as performed in a greenhouse in De Kwakel, The Netherlands, shows that the aforementioned characteristics and distinctions come true to form and are established and transmitted through succeeding propagations.

BRIEF DESCRIPTION OF THE DRAWING

The new variety of rose plant is illustrated by the accompanying photographic illustration, which shows typical specimens of the flowers of the new variety in different stages of development and as depicted in color as nearly true as is reasonably possible to attain In illustrations of this type.

BOTANICAL DESCRIPTION OF THE PLANT

Botanical: Rosa L. cv. 'Selquest'.

The following is a detailed description of this new variety, with color terminology in accordance with The Royal Horticultural Society Colour Chart (R.H.S.C.C.). The terminology used in the color description herein refers to plate numbers in the aforementioned color chart e.g "55C" is plate "55C" of The Royal Horticultural Society Colour Chart.

Observations are made from specimens grown in a greenhouse in De Kwakel, The Netherlands, on a one year old plant. The color values were determined at 14:00 pm on Nov. 26 2002 under artificial light at De Kwakel. The following traits have been repeatedly observed and are determined to be basic characteristics of 'Selquest', which In combination distinguish this Rosa as a new and distinct cultivar.

INFLORESCENCE

Blooming habit of 'Selquest': Almost continuous.
Time of beginning of flowering: Early.

A. Bud:

*Size.*—Large. Diameter 3.0–3.5 cm. Length 5.0–5.5 cm.

*Form.*—Ovoid.

*Color.*—When the sepals first divide, the color of the outside is red, RHS 53A.

*Sepals.*—Length: 40 to 45 mm. Hooded over. Curl back when open. Color: inside: green, RHS 147C. outside: green, RHS 144A. Hairs on Inner surface: many. On outer surface: none.

*Phyllaries.*—Number: 2 to 6, average 4. Shape: elliptic, 15×4 mm. Color: green, RHS 137A.

*Calyx.*—Color: light green, RHS 144B. Shape: funnelshaped. Size: medium: diameter: 9–10 mm. Aspect: smooth. Odor when rubbed: slightly present.

*Rate of opening.*—Normal.

*Peduncle.*—Length: long (10–11 cm). Aspect: a little bit hairy. Strength: medium. Color: light green, RHS 144B.

*Openings.*—Opens up completely; is not affected by adverse weather.

B. Bloom:

*Size.*—Very large; When fully expanded about 11 cm in diameter with a depth of about 5.5 cm.
*Borne.*—Single.
*Stems.*—Length: 90–120 cm. Strength: medium.
*Form* (*when first open*).—Round. Permanence: good.
*Petalage.*—Number of petals: 35–40.
*Color.*—Center of flower: red, RHS 45A. Outer petals: red, RHS 45A. Base of petals: red, RHS 45A. Spot at the base: present, yellow RHS 13A. Inside of petals: red, RHS 45A. Reverse of petals: red, RHS 53A. General tonality: red, RHS 45A.
*Discoloration.*—General tonality is not changing when aging.

C. Petals:
*Texture.*—Soft; is not affected by wet or hot weather.
*Appearance.*—Inside: satiny. Outside: shiny.
*Form.*—Obovate. Reflexing of margin: medium. Undulation of margin: medium.
*Arrangement.*—Regular.
*Petaloids in center.*—Number: 2. Size: medium. Color: base red RHS 53A. middle and marginal zone red RHS 53A.
*Persistence.*—Drops off cleanly.
*Fragrance.*—Medium sweet scent.
*Lasting quality.*—On the plant: 14–17 days. As cut-flower: 12–15 days.

REPRODUCTIVE ORGANS

A. Stamens:
*Arrangement.*—Regular.
*Number.*—Average close to 80.
*Length.*—10 to 14 mm.
*Anthers.*—Size: large (2 to 3 mm). Color: yellow-orange RHS 17A.
*Filaments.*—Length: medium (8–11 mm). Color: base of anthers: yellow (1–2 mm) RHS 5A. lower filament: dark red RHS 46A.
*Pollen.*—Color: yellow, RHS 2B.

Pistils:
*Styles.*—Number: average close to 40. Length: 9 to 11 mm. Color: lower part (80%) cream white RHS 4D, upper part red RHS 42A.
*Stigmas.*—Color: light yellow, RHS 11B.
*Fruit.*—Fertility: normal. Shape: round. Color at maturity: orange, RHS 24B.

PLANT

A. Form: Bed rose.
B. Growth: Upright.
C. Height: High (100–150 cm).
D. Width: Medium (30–35 cm).
E. Foliage: 11 to 13 compound leaves on bloom stem.
*Size.*—Large.
*Quantity.*—Average.
*Color.*—New foliage: upper side: red brown, RHS 183A. under side: brown, RHS 178A. Old foliage: upper side: dark green, RHS 147A. Under side: green, RHS 148A.
*Texture.*—Upper side: leathery. Under side: dull.
*Terminal leaflet.*—Shape: broad elliptic, base obtuse. Size: large. Length: 90–100 mm. Diameter: 65–69 mm. Length petiole: 29–31 mm.
*Ribs and veins.*—Anthocyan colored, RHS 174B.
*Rachis.*—Upper side: red brown, RHS 176A. Lower side: green, RHS 144A.
*Margin type.*—Medium serrate, 3 points/cm, 2 mm peak.
*Stipules.*—Length: 20 mm, auricle 5 to 6 mm. Texture: smooth. Color: green, RHS 143A.

F. Resistance to diseases: Normal resistance to common diseases.
G. Drought tolerance: Normal.
H. Heat tolerance: Normal.
I. Wood:
*New wood.*—Color: red brown, RHS 177A. Bark: smooth.
*Old wood.*—Color: dark green, RHS 144A. Bark: smooth.

J. Thorns:
*Quantity.*—Medium. On main stalks from base: medium. On laterals from stalk: medium.
*Form.*—Deep concave.
*Length.*—Thin, large (6–8 mm).
*Hooked.*—Downward.
*Color* (*when young*).—Red brown, RHS 176A.
*Position.*—Irregular.

K. Prickles:
*Quantity.*—Absent or very few. On peduncle: absent. On rachis: very few, on average 3 per compound leaf.

L. Short needles:
*Quantity.*—very few on peduncle.

I claim:

1. A new and distinct cultivar of Rosa plant named 'Selquest' of the Hybrid Tea class, substantially as herein shown and described, characterized by its continuous production of very large flowers and flowerbuds of a persistent red color not affected by climatical changes, having a very good presentation in bud as well as open flower, borne singly on upright long stems and showing vigorous growth of the plants, especially adapted to the South American climate and the specified characteristics enumerated above. * * * * *

* * * * *

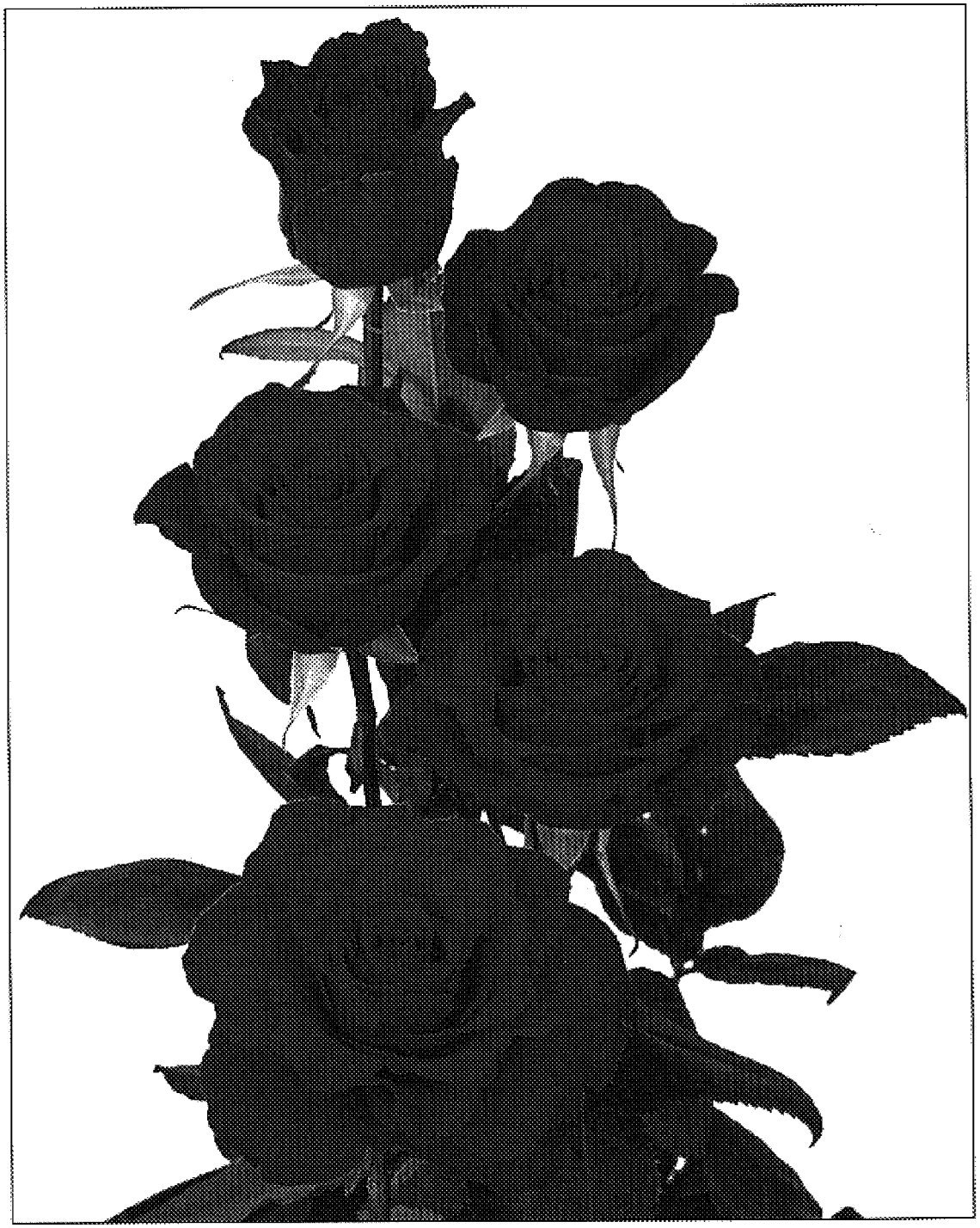

Title of invention: Rosa plant named 'Selquest'